United States Patent [19]

Kissinger

[11] Patent Number: 5,382,708
[45] Date of Patent: Jan. 17, 1995

[54] PROCESS FOR INHIBITING DIHYDRIC PHENOL DEGRADATION AND COLOR FORMATION AND COMPOSITION THEREOF

[75] Inventor: Gaylord M. Kissinger, Evansville, Ind.

[73] Assignee: General Electric Company, Pittsfield, Mass.

[21] Appl. No.: 146,353

[22] Filed: Oct. 29, 1993

[51] Int. Cl.$^6$ .................... C07C 37/00; C07C 37/68; C07C 37/16

[52] U.S. Cl. .................... 568/702; 568/701; 568/724; 568/763

[58] Field of Search .............. 568/702, 724, 763, 701, 568/703

[56] References Cited

U.S. PATENT DOCUMENTS

| | | |
|---|---|---|
| 2,999,835 | 9/1961 | Goldberg ............... 568/702 |
| 3,028,365 | 4/1962 | Schnell et al. ........... 568/702 |
| 3,334,154 | 8/1967 | Kim ..................... 568/702 |
| 4,131,575 | 12/1978 | Adelmann et al. ........ 560/17.4 |
| 4,847,433 | 7/1989 | Kissinger ............... 568/727 |
| 4,876,391 | 10/1989 | Kissinger ............... 568/724 |
| 4,902,836 | 2/1990 | Kissinger ............... 568/702 |
| 5,185,475 | 2/1993 | Kissinger ............... 568/748 |

Primary Examiner—Werren B. Lone

[57] ABSTRACT

A process for improving the color of bisphenol-A and improving yields of bisphenol-A comprises the addition of hypophosphorus acid either prior to or concurrent with a distillation step.

16 Claims, No Drawings

PROCESS FOR INHIBITING DIHYDRIC PHENOL DEGRADATION AND COLOR FORMATION AND COMPOSITION THEREOF

FIELD OF THE INVENTION

The present invention relates to a process for inhibiting the formation of undesired colored contaminating products during process steps involving thermal treating or distillation where 4,4″-(dihydroxyphenyl)propane-2 is present.

BACKGROUND OF THE INVENTION

The dihydric phenols have achieved significant success in their commercial applications. Dihydric phenols are useful in the commercial manufacture of various polymers including the polyarylates, polyamides, epoxides, polyetherimides, polysulfones, and the polycarbonates. Significant attention has been directed to the commercial preparation of the dihydric phenols. For many years it has been well known that the acid catalyzed reaction of phenol with specific aldehydes or ketones could prepare the 4,4′-dihydric phenol with specific groups derived from the aldehyde or ketone connecting the two phenolic rings. In particular when the phenol is reacted with acetone, the dihydric phenol 4,4′(dihydroxyphenyl)propane-2, hereafter referred to as bisphenol-A, is formed. This compound has particular utility in the synthesis and preparation of polycarbonates, polyarylates, and copolyestercarbonates as well as epoxies. In order to manufacture certain polymers, in particular the polycarbonates, the bisphenol-A must have a high level of freedom from impurities. In particular, this freedom from impurities must manifest itself as a freedom from impurities imparting an undesirable color either to the bisphenol-A or the products manufactured therefrom.

Additionally, since the process to manufacture bisphenol-A contributes substantially to the final cost of products manufactured therefrom, the process should be particularly efficient. Consequently much attention has been directed to the recovery of bisphenol-A after its preparation. Because of the economic factors involved, recovery of bisphenol-A from every process stream where it occurs can be significant in terms of increasing the yield of bisphenol-A and also reducing its cost. Thus various side- or purge-streams have been evaluated for their potential in terms of recovery of bisphenol-A.

In the down stream processing of the composition resulting from the acid catalyzed condensation reaction, a loss in the quantity of the desired dihydric phenol and a reduction in the quality of the color of the dihydric phenol composition has been observed when mixtures of the desired dihydric phenol, phenol, and isomers of the desired dihydric phenol are separated in conventional distillation trains to recover the desired dihydric phenol. Generally, without an additive, portions of these materials readily degrade to a very dark color and undergo substantial chemical transformation which is viewed in the context of its ultimate application as a degradation in quality. When this occurs, significant reductions in the quantity of recoverable desired dihydric phenol are observed.

It has now been found that this degradation of the desired dihydric phenol, usually bisphenol-A, as well as the formation of undesired colored impurities can be substantially inhibited by the addition of hypophosphorous acid, $H_3PO_2$, to the composition comprising dihydric phenol, phenol, and isomers of dihydric phenol prior to or concurrent with the distillation step.

SUMMARY OF THE INVENTION

In accordance with the invention, there is a process which comprises the addition of a dihydric phenol degradation inhibiting and color inhibiting effective amount of hypophosphorous acid to a composition comprising a dihydric phenol, phenol, and isomers of the dihydric phenol, said addition occurring prior to or concurrent with a distillation procedure.

A further aspect of the invention is a composition comprising dihydric phenol, phenol, and isomers of the dihydric phenol in admixture with a dihydric phenol degradation inhibiting and color inhibiting effective amount of hypophosphorous acid.

DETAILED DESCRIPTION OF THE INVENTION

The most well-known dihydric phenol is bisphenol-A. The invention is further described in detail with the production of bisphenol-A. Other dihydric phenols are expected to have the color and loss problems associated with bisphenol-A, if made from the acid catalyzed condensation of a phenol with an aldehyde or ketone. Examples of such dihydric phenols may be found in U.S. Pat. No. 2,999,835; 3,028,365; 3,334,154, and 4,131,575.

Phenol and acetone are passed into a reactor having an acidic catalyst system. In place of the previously used hydrochloric acid catalyst, solid ion exchange resins are now used as the acid catalyst with a consequent reduction in problems associated with the acid catalyzed corrosion of the steel reactors. Such a solid ion exchange resin is usually an Amberlite ®-type resin obtained for example from Rohm and Haas. This resin has a styrenic backbone with pendant SO3H groups that provide an acidic character to the resin. Usually the styrenic backbone is cross-linked with a small quantity of divinyl benzene or other cross linking reagent. The addition of a cross linking agent provides structural strength and rigidity to the catalyst. While other ion exchange resins have been used, the art generally prefers the use of resins possessing a styrenic backbone cross linked with a difunctional monomer and having SO3H groups that are pendant from the aromatic nucleus of the styrene moiety. The phenol, in excess for purposes of mass action effects on the reaction, together with the acetone is passed over the acidic ion exchange resin. After reaction, the bisphenol-A in the product stream can be recovered using a distillation train wherein the components bisphenol-A, phenol, and isomers of dihydric phenol are separated via their respective differences in boiling points. Because these phenolic compounds have high boiling points at atmospheric pressure, these distillations are typically performed under vacuum Alternatively, after preparation the bisphenol-A can be initially separated by the formation of a phenol bisphenol-A adduct. This eliminates the separation by distillation of a major portion of the bisphenol-A product. However, minor portions of bisphenol-A in the purge streams may be recovered by distillation.

In each of these processes, loss in the yield of bisphenol-A and an increase in the color is observed after distillation. The addition of hypophosphorous acid to the mixture of dihydric phenol, phenol, and isomers of dihydric phenol bring about a significant reduction in the observed losses. Hypophosphorous acid has the formula H3PO2. Previously, the addition of phosphonite esters as taught in U.S. Pat. No. 4,902,836 herewith incorporated by reference has shown beneficial effects in preventing losses of bisphenol-A. The phosphonite esters of the 836 patent are neither protic acids nor hydroxidic bases.

Generally from about 0.005 to about 0.05 weight percent of the hypophosphorous acid based upon the dihydric phenol, phenol, and the isomeric dihydric phenol composition is sufficient to bring about reduction in dihydric phenol loss and color. Below its minimum very little effect is observed. Above this maximum, the additional effects generated are typically very minor and are usually offset by the increased cost. A preferred quantity of hypophosphorous acid is from about 0.01 to about 0.30 weight percent.

EXAMPLES

The following examples are intended to illustrate the general inventive concept and not to limit same. In the examples, the composition includes the following materials, p,p'BPA is bisphenol-A o,p' is the ortho-para isomer of bisphenol-A, "dimer" is IPP dimers, BPX-1 is a trisphenol, CR-1 is chroman-1, "spiro" is spirobiindane, IPP is isopropenylphenol, BPX-II is a further trisphenol.

The distillation proceeds at 210° C. At this temperature, phenol is distilled overhead while the bisphenol-A remains in the bottoms. The original composition and bottoms after distillation are analyzed by liquid chromatography. The color of the bottoms after distillation of the phenol is measured by dissolving a standard sample size in a standard amount of methanol and measuring the ultraviolet absorbance at 350 nm, the so-called tar factor, TF. The lower the absorbancy number the lower the color, it is preferred to have the absorbancy number as low as possible. A second color analysis is also made, the initial yellowness index, IYI, taken by measuring the visible spectrum of a standardized sample in methanol against a pure methanol reference. The first distillation, control, has no additive. The second distillation has an effective amount of the hypophosphorous acid. All the numbers in the tables are in grams except where absorption or absorbancy numbers are reported.

| Example 1 | Starting Material | Control No Additive | Additive 100 ppm H3PO2 |
|---|---|---|---|
| TF | 6.1 | 24.7 | 21.8 |
| IYI | 12.7 | 40.7 | 29.0 |
| Weights (gm's) | | | |
| Phenol | 271.84 | 89.94 | 75.79 |
| IPP | 0.002 | 0.158 | 0.163 |
| p,p'BPA | 117.482 | 106.680 | 112.30 |
| o',p,BPA | 5.433 | 6.170 | 6.710 |
| Dimers | 0.816 | 1.020 | 1.060 |
| BPX-4 | 0.764 | 0.828 | 0.882 |
| Cr-1 | 1.010 | 1.200 | 1.290 |
| Spiro | NDA | NDA | NDA |
| BPX-II | 0.363 | 0.461 | 0.494 |
| Unknowns | 2.220 | 2.230 | 2.290 |
| % BPA Loss | NA | 9.19% | 4.41% |

| Example 2 | Starting Material | Control No Additive | Additive 100 ppm H3PO2 |
|---|---|---|---|
| TF | 7.51 | 16.4 | 13.8 |
| IYI | 16.3 | 32.2 | 22.5 |
| Weights (gm's) | | | |
| Phenol | 294.840 | 77.460 | 81.54 |
| IPP | NDA | 0.202 | 0.166 |
| p,p'BPA | 98.040 | 91.69 | 93.560 |
| o',p,BPA | 4.720 | 5.540 | 5.710 |
| Dimers | 0.152 | 0.219 | 0.218 |
| BPX-I | 0.580 | 0.795 | 0.787 |
| Cr-1 | 0.192 | 0.219 | 0.232 |
| Spiro | 0.156 | 0.014 | 0.012 |
| BPX-II | NDA | 0.008 | 0.009 |
| Unknowns | 1.260 | 1.040 | 0.956 |
| % BPA Loss | NA | 6.48% | 4.57% |

| Example 3 | Starting Material | Control No Additive | Additive 100 ppm H3PO2 |
|---|---|---|---|
| TF | 6.19 | 17.7 | 15.6 |
| IYI | 15.7 | 29.0 | 22.0 |
| Weights (gm's) | | | |
| Phenol | 297.100 | 100.910 | 77.360 |
| IPP | 0.003 | 0.145 | 0.129 |
| p,p'BPA | 95.000 | 77.160 | 94.700 |
| o',p,BPA | 5.390 | 4.370 | 5.720 |
| Dimers | 0.228 | 0.221 | 0.289 |
| BPX-I | 0.720 | 0.578 | 0.711 |
| Cr-1 | 0.344 | 0.264 | 0.336 |
| Spiro | 0.012 | 0.010 | 0.012 |
| BPX-II | 0.052 | 0.049 | 0.072 |
| Unknowns | 1.110 | 0.995 | 1.320 |
| % BPA Loss | NA | 18.78% | 0.32% |

| Example 4 | Starting Material | H3PO2 Additive (ppm) | | | |
|---|---|---|---|---|---|
| | | 100 | 50 | 25 | 10 |
| TF | 3.37 | 10.6 | 11.7 | 11.9 | 13.1 |
| IYI | 6.6 | 15.7 | 21.0 | 22.6 | 24.3 |
| Weights (gm's) | | | | | |
| Phenol | 309 | 54.0 | 64.0 | 61.0 | 64.0 |
| IPP | NDA | 0.15 | 0.12 | 0.13 | 0.16 |
| p,p'BPA | 78.6 | 82.0 | 83.5 | 81.5 | 82.4 |
| o',p,BPA | 9.00 | 5.90 | 6.20 | 5.90 | 6.00 |
| Dimers | 0.22 | 0.13 | 0.19 | 0.18 | 0.18 |
| BPX-I | 1.06 | 0.78 | 0.79 | 0.76 | 0.81 |
| Cr-1 | 0.37 | 0.23 | 0.24 | 0.23 | 0.23 |
| Spiro | 0.03 | 0.02 | 0.02 | 0.01 | 0.02 |
| BPX-II | 0.02 | 0.01 | 0.01 | 0.01 | 0.01 |
| Unknowns | 1.58 | 0.95 | 0.98 | 0.94 | 0.94 |

Note: The data presented in the Table for Example 4 have been rounded to facilitate textual presentation.

EXAMPLE 5

Hypophosphorous acid was added at a rate of 87.5 ppm to an operating bisphenol-A plant stream that feeds the phenol distillation step in a bisphenol-A process train. The residence time of this system is such that the effects of the addition should be expected within 12 hours in the product of the distillation step, and 24 hours for the effect on p,p'BPA final product quality following the final purification step. The following table shows the before and after effect of hypophosphorous acid addition and p,p'BPA content of the product from the distillation step.

| | | Plant Data A | |
|---|---|---|---|
| Date | Time | Tar Factor Distillation Product | bisphenol-A Content (Wt %) Distillation Product |
| Day 1 | 01:00 | 25.9 | 91.67 |
| Day 1 | 08:15 | 16.6 | 92.45 |
| Day 1 | 17:00 | 26.8 | 91.85 |
| Day 2 | 01:00 | 29.9 | 91.82 |
| Average Values | | 24.8 | 91.94 |
| Hypophosphorous acid added to process | | | |
| Day 2 | 08:30 | 5.2 | 92.66 |
| Day 2 | 13:00 | 5.2 | 92.38 |
| Day 2 | 17:00 | 5.6 | 92.01 |
| Day 3 | 09:00 | 7.6 | 92.17 |
| Average values | | 5.9 | 92.30 |

The following data indicate the before and after effect of adding hypophosphorous acid on final product bisphenol-A color and composition, following the final process purification step. Residual levels of hypophosphorous acid are detectable in the bisphenol-A and in the polycarbonate resins made from bisphenol-A treated with hypophosphorous acid; such detection of residual phosphorus levels is dependent upon the amount of hypophosphorous acid initially added, the method of analysis, and the resolution of the method of analysis.

| | | Plant Data B | |
|---|---|---|---|
| Date | Time | Tar Factor Final Product Bisphenol-A | bisphenol-A Content (Wt %) Final Product Bisphenol-A |
| Day 1 | 17:00 | 3.5 | 99.44 |
| Day 2 | 01:00 | 4.5 | 99.48 |
| Day 2 | 17:00 | 3.9 | 99.45 |
| Day 2 | 18:30 | 2.6 | 99.88 |
| Average Values | | 3.6 | 99.56 |
| Hypophosphorous acid added to process | | | |
| Day 2 | 17:00 | 2.3 | 99.87 |
| Day 3 | 01:00 | 1.1 | 99.89 |
| Day 3 | 05:00 | 1.7 | 99.63 |
| Day 3 | 09:00 | 1.7 | 99.89 |
| Average values | | 1.7 | 99.82 |

In all of the experiments reported as a reduction to practice and demonstration of the inventive concepts herein embodied, the hypophosphorous acid was added as a 50 weight percent aqueous solution. In all of the forgoing examples the loss of bisphenol-A is reduced and the color degradation is minimized. Thus the purification of bisphenol-A by distillation is substantially improved by the addition of hypophosphorous acid. The addition of hypophosphorous acid will leave residues of phosphorus in the bisphenol-A and the polycarbonate resins manufactured therefrom such that polycarbonate resins manufactured using bisphenol-A improved by the process of the present invention may have up to 20 ppm phosphorus.

Having described the invention, that which is claimed is:

1. A process for the purification of bisphenol-A comprising the addition of an effective amount of hypophosphorous acid and a distillation.

2. The process of claim 1 wherein the amount of hypophosphorous acid ranges from about 5 ppm to about 200 ppm.

3. The process of claim 1 wherein the amount of hypophosphorous acid ranges from about 0.005 weight per cent to about 0.05 weight percent.

4. The process of claim 1 wherein the steps of hypophosphorous acid addition and distillation are sequential.

5. The process of claim 1 wherein the steps of hypophosphorous acid addition and distillation are concurrent.

6. The process of claim 4 wherein the amount of hypophosphorous acid ranges from about 0.005 weight per cent to about 0.05 weight percent.

7. The process of claim 4 wherein the amount of hypophosphorous acid ranges from about 5 ppm to about 200 ppm.

8. The process of claim 5 wherein the amount of hypophosphorous acid ranges from about 0.005 weight per cent to about 0.05 weight percent.

9. The process of claim 5 wherein the amount of hypophosphorous acid ranges from about 5 ppm to about 200 ppm.

10. The process of claim 1 wherein the amount of hypophosphorous acid ranges from about 0.01 weight per cent to about 0.30 weight percent.

11. The process of claim 10 wherein the steps of hypophosphorous acid addition and distillation are sequential.

12. The process of claim 10 wherein the steps of hypophosphorous acid addition and distillation are concurrent.

13. The process of claim 1 wherein a bisphenol-A product is produced having a tar factor color measurement below about 10.

14. An improved polycarbonate resin wherein the improvement comprises preparing a polycarbonate from a bisphenol-A reagent having an improved color wherein said color is below a tar factor color measurement of about 10 and wherein said color improvement is produced by the process of claim 1.

15. The improved polycarbonate resin of claim 14 wherein said polycarbonate contains a phosphorus residue from hypophosphorous acid.

16. The improved polycarbonate resin of claim 14 wherein said polycarbonate contains a phosphorus residue from hypophosphorous acid said phosphorus residue being below about 20 ppm.

* * * * *